US00PP33731P2

(12) United States Plant Patent
Koot

(10) Patent No.: US PP33,731 P2
(45) Date of Patent: Dec. 7, 2021

(54) ***SCAEVOLA* PLANT NAMED 'DOSCASCAPUBI'**

(50) Latin Name: *Scaevola aemula*
Varietal Denomination: Doscascapubi

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/242,239

(22) Filed: Apr. 27, 2021

(51) Int. Cl.
*A01H 5/02* (2018.01)

(52) U.S. Cl.
USPC ..... Plt./363

(58) Field of Classification Search
USPC ..... Plt./363
See application file for complete search history.

*Primary Examiner* — Annette H Para
(74) *Attorney, Agent, or Firm* — C. Anne Whealy

(57) ABSTRACT

A new and distinct cultivar of *Scaevola* plant named 'Doscascapubi', characterized by its mounding to outwardly spreading plant habit; freely branching habit; early and freely flowering habit; long flowering period; flowers that are purple in color; and good container and garden performance.

1 Drawing Sheet

Botanical designation: *Scaevola aemula.*
Cultivar denomination: 'DOSCASCAPUBI'.

STATEMENT REGARDING PRIOR DISCLOSURES BY INVENTOR/APPLICANT & ASSIGNEE

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Scaevola* plant, botanically known as *Scaevola aemula* and hereinafter referred to by the name 'Doscascapubi'.

The new *Scaevola* plant a product of a planned breeding program conducted by the Inventor in Rheinberg, Germany. The objective of the breeding program is to create new compact, mounding and early-flowering *Scaevola* plants with numerous attractive flowers.

The new *Scaevola* plant originated from a cross-pollination in Rheinberg, Germany in July, 2019 of a proprietary selection of *Scaevola aemula* identified by the code number CC17-000507-001, not patented, as the female, or seed, parent with a proprietary selection of *Scaevola aemula* identified as code number CC17-001911-001, not patented, as the male, or pollen, parents. The new *Scaevola* plant was discovered and selected by the Inventor as a single flowering plant from within the progeny of the stated cross-pollination in a controlled greenhouse environment in Rheinberg, Germany in May, 2020.

Asexual reproduction of the new *Scaevola* plant by vegetative tip cuttings in a controlled greenhouse environment in Rheinberg, Germany since June, 2020 has shown that the unique features of this new *Scaevola* plant are stable and reproduced true to type in successive generations.

SUMMARY OF THE INVENTION

Plants of the new *Scaevola* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Doscascapubi'. These characteristics in combination distinguish 'Doscascapubi' as a new and distinct *Scaevola* plant:

1. Mounding to outwardly spreading plant habit.
2. Freely branching habit.
3. Early and freely flowering habit.
4. Long flowering period.
5. Flowers that are purple in color.
6. Good container and garden performance.

Plants of the new *Scaevola* can be compared to plants of the female and male parent selections. Plants of the new *Scaevola* differ primarily from plants of the parent selections in flower color as plants of the new *Scaevola* have purple-colored flowers whereas plants of the parent selections are pink in color.

Plants of the new *Scaevola* can be compared to plants of the *Scaevola aemula* 'Purple Haze', not patented. In side-by-side comparisons, plants of the new *Scaevola* differ from plants of the 'Purple Haze' in the following characteristics:

1. Plants of the new *Scaevola* are shorter and broader than plants of 'Purple Haze'.
2. Plants of the new *Scaevola* have broader leaves than plants of 'Purple Haze'.
3. Plants of the new *Scaevola* are more freely flowering than plants of 'Purple Haze'.

4. Plants of the new *Scaevola* have larger flowers than plants of 'Purple Haze'.

BRIEF DESCRIPTION OF THE PHOTOGRAPH

The accompanying colored photograph illustrates the overall appearance of the new *Scaevola* plant showing the colors as true as it is reasonably possible to obtain in colored reproductions of this type. Colors in the photograph may differ slightly from the color values cited in the detailed botanical description which accurately describe the colors of the new *Scaevola* plant. The photograph is a close-up view of a typical flowering plant of 'Doscascapubi'.

DETAILED BOTANICAL DESCRIPTION

The aforementioned photograph and following observations and measurements describe plants grown during the spring and early summer in 22-cm containers in a glass-covered greenhouse in Rheinberg, Germany and under cultural practices typical of commercial *Scaevola* production. During the production of the plants, day and night temperatures averaged 18° C. and light levels averaged 4,500 lux. Plants were pinched one time about three weeks after planting. Plants were twelve weeks old when the photograph was taken and 25 weeks old when the description was taken. In the following description, color references are made to The Royal Horticultural Society Colour Chart, Fifth Edition, except where general terms of ordinary dictionary significance are used.

Botanical classification: *Scaevola aemula* 'Doscascapubi'.

Parentage:

*Female, or seed, parent.*—Proprietary selection of *Scaevola aemula* identified as code number CC17-000507-001, not patented.

*Male or pollen parent.*—Proprietary selection of *Scaevola aemula* identified as code number CC17-001911-001, not patented.

Propagation:

*Type.*—By vegetative tip cuttings.

*Time to initiate roots, summer.*—About five days at temperatures about 20° C.

*Time to initiate roots, winter.*—About seven days at temperatures about 20° C.

*Time to develop roots, summer.*—About three weeks at temperatures about 20° C.

*Time to develop roots, winter.*—About four weeks at temperatures about 20° C.

*Root description.*—Fine, fibrous; typically close to 162C in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Mounding to outwardly spreading plant habit; moderately vigorous growth habit and moderate growth rate.

*Branching habit.*—Freely branching habit with about eight primary lateral branches each with about six secondary lateral branches developing per plant; pinching enhances branching potential.

*Plant height.*—About 22 cm.

*Plant diameter (area of spread).*—About 60 cm.

Lateral branch description:

*Length.*—About 70 cm.

*Diameter.*—About 5 mm.

*Internode length.*—About 5 cm.

*Aspect.*—Mostly outwardly.

*Texture and luster.*—Smooth, glabrous; matte.

*Color, developing.*—Close to 144A tinged with close to 200C.

*Color, developed.*—Close to 146A.

Leaf description:

*Arrangement.*—Alternate, simple.

*Length.*—About 3.8 cm.

*Width.*—About 1.6 cm.

*Shape.*—Spatulate.

*Apex.*—Acute.

*Base.*—Attenuate.

*Margin.*—Dentate; incisions relatively shallow in depth and divergent.

*Texture and luster, upper and lower surfaces.*—Smooth, glabrous; matte.

*Venation pattern.*—Pinnate.

*Color.*—Developing leaves, upper surface: Close to 147A tinged with close to 200B. Developing leaves, lower surface: Close to 147B. Fully expanded leaves, upper surface: Close to 147A; venation, close to 144A. Fully expanded leaves, lower surface: Close to 146B; venation, close to 144B.

*Petioles.*—Length: About 3.8 mm. Diameter: About 2 mm. Strength: Moderately strong. Texture and luster: Smooth, glabrous; semi-glossy. Color, upper surface: Close to 144A. Color, lower surface: Close to 144B.

Flower description:

*Flower type and shape.*—Zygomorphic, semi-circular, fan-shaped flowers with five petals fused at the base to form a tubular flower throat; flower throat open along the upper surface exposing the reproductive organs.

*Flower arrangement and quantity.*—Solitary sessile flowers arising from upper leaf axils; flowers mostly horizontal; freely flowering habit with typically about 1510 flowers per plant developing during the flowering season.

*Flowering time.*—Early flowering habit, plants begin flowering after about six weeks after planting; long flower period, plants flower continuously from spring into the late summer in Northern Europe.

*Flower longevity.*—Flowers typically last about five to seven days on the plant; flowers not persistent.

*Fragrance.*—None detected.

*Flower buds.*—Length: About 1.7 cm. Diameter: About 2.5 mm. Shape: Ensiform. Texture and luster: Smooth, glabrous; matte. Color: Close to 148B and 83C.

*Flowers.*—Diameter: About 1.5 cm by 2.7 cm. Depth: About 2.6 cm. Throat diameter: About 3 mm. Tube length: About 1.1 cm. Tube diameter: About 3 mm.

*Petals.*—Quantity per flower: Five, fused at base. Length, beyond tube: About 1.2 cm. Width, beyond tube: About 5 mm. Shape: Narrowly elliptic. Apex: Acute. Margin: Entire; not undulate. Texture and luster, upper and lower surfaces: Smooth, glabrous; matte. Texture, throat: Smooth, glabrous. Texture, tube: Pubescent; rough. Color: When opening, upper surface: Close to N87A. When opening, lower surface: Close to N87B. Fully opened, upper surface: Close to N87A; towards the base, close to 2A; venation, close to 83A; color becoming closer to N88B with subsequent development. Fully opened, lower surface: Close to N87C; venation, close to 83A; color becoming closer to N88C with subsequent development. Throat: Close to 151B and 2A; venation, close to 83A. Tube: Close to 151C; venation, close to 83A.

*Sepals.*—Quantity per flower: One large and two smaller sepals fused at the base. Length, larger sepal: About 1.3 cm. Length, smaller sepals: About 5.7 mm. Width, larger sepal: About 4.8 mm. Width, smaller sepals: About 0.9 mm. Shape, all sepals: Lanceolate. Apex, all sepals: Acute. Margin, all sepals: Entire. Texture and luster, all sepals, upper and lower surfaces: Pubescent, rough; matte. Color, upper surface: Close to 146A. Color, lower surface: Close to 146B.

*Reproductive organs.*—Androecium: Stamen quantity per flower: Five or six. Filament length: About 4 mm. Filament color: Close to 157D. Anther size: About 0.2 mm by 1.5 mm. Anther shape: Ellipsoidal. Anther color: Close to 160B. Pollen: Sparse. Pollen color: Close to 4C. Gynoecium: Pistil quantity per flower: One. Pistil length: About 1.3 cm. Style length: About 1 cm. Style color: Close to N79A. Stigma diameter: About 2 mm. Stigma shape: Oblate. Stigma color: Close to 155A. Ovary color: Close to 144C.

*Fruits.*—Quantity per plant: About 100. Length: About 3 mm. Diameter: About 1.4 mm. Texture: Rough. Color: Close to 203B.

*Seeds.*—Quantity per fruit: One. Length: About 2.8 mm. Diameter: About 1.2 mm. Texture: Smooth, glabrous. Color: Close to 200A.

Garden performance: Plants of the new *Scaevola* have been observed to have good garden performance and to tolerate rain, wind and temperatures ranging from about 3° C. to about 40° C. and to be suitable for USDA Hardiness Zone 11.

Pathogen & pest resistance: To date, plants of the new *Scaevola* have not been shown to be resistant to pathogens and pests common to *Scaevola* plants.

It is claimed:

1. A new and distinct *Scaevola* plant named 'Doscascapubi' as illustrated and described.

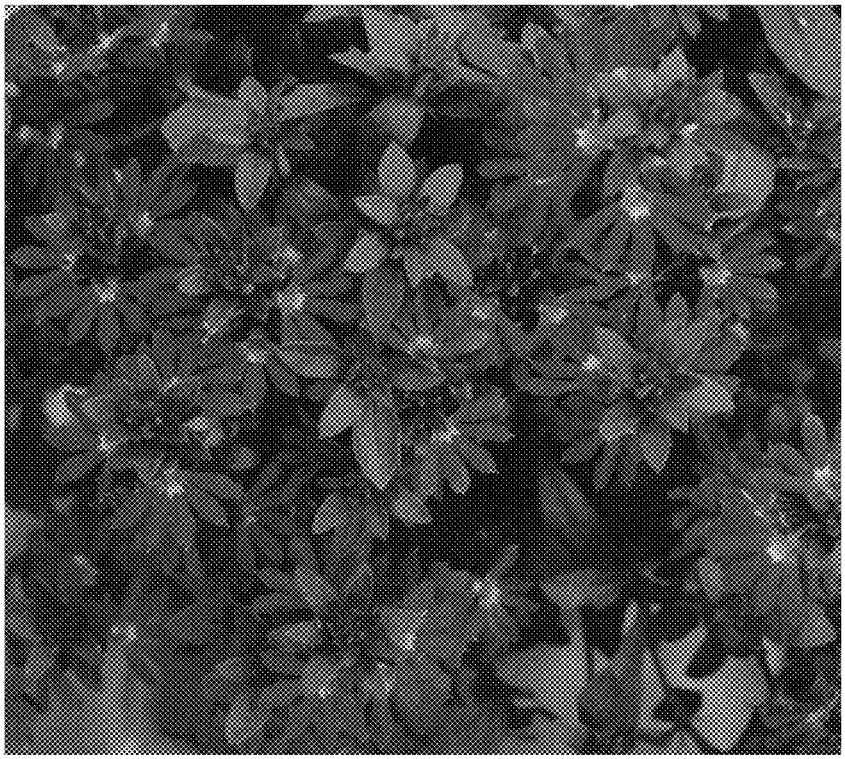

* * * * *